(12) United States Patent
Hayashi et al.

(10) Patent No.: US 12,324,822 B2
(45) Date of Patent: Jun. 10, 2025

(54) METHOD OF TREATING TYPE 2 DIABETIC PATIENTS

(71) Applicant: OSATO INTERNATIONAL INC., Gifu (JP)

(72) Inventors: Yukiyasu Hayashi, Gifu (JP); Chandan K. Sen, Columbus, OH (US)

(73) Assignee: Osato International Inc., Gifu (JP)

( * ) Notice: Subject to any disclaimer, the term of this patent is extended or adjusted under 35 U.S.C. 154(b) by 88 days.

(21) Appl. No.: 17/117,647

(22) Filed: Dec. 10, 2020

(65) Prior Publication Data

US 2021/0299200 A1    Sep. 30, 2021

Related U.S. Application Data

(63) Continuation of application No. 15/062,912, filed on Mar. 7, 2016, now abandoned, which is a continuation of application No. PCT/JP2014/071810, filed on Aug. 20, 2014.

(51) Int. Cl.
*A61K 36/185* (2006.01)
*A61K 36/06* (2006.01)
*A61P 3/10* (2006.01)

(52) U.S. Cl.
CPC ............ *A61K 36/185* (2013.01); *A61K 36/06* (2013.01); *A61P 3/10* (2018.01); *A61K 2236/19* (2013.01)

(58) Field of Classification Search
CPC .................................................. A61K 36/185
See application file for complete search history.

(56) References Cited

U.S. PATENT DOCUMENTS

2016/0184377 A1\* 6/2016 Hayashi ............... A61P 3/10
424/278.1

FOREIGN PATENT DOCUMENTS

| JP | 2005-341964 A | 12/2005 |
| JP | 2008-199931 A | 9/2008 |
| JP | 2011-041478 A | 3/2011 |

OTHER PUBLICATIONS

Dickerson et al. Antioxidants & Redox Signaling, 2015, 22(4):339-345.\*

(Continued)

*Primary Examiner* — Daniel E Kolker
*Assistant Examiner* — Maureen Varina Driscoll
(74) *Attorney, Agent, or Firm* — Morgan, Lewis & Bockius LLP (57) ABSTRACT

The present disclosure provides a method of promoting respiratory burst in a subject with type 2 diabetic, comprising orally administering an effective amount of fermented papaya preparation (FFP) with carbohydrate, protein lipid, potassium, and water.

11 Claims, 4 Drawing Sheets

(56) References Cited

OTHER PUBLICATIONS

FPP sachet Data, 1 page.*
Collard and Roy. Improved Function of Diabetic Wound-Site Macrophages and Accelerated Wound Closure in Response to Oral Supplemental of a Fermented Papaya Preparation, Antioxidants & Redoc Signaling, 13(5):599-606. (Year: 2010).*
Aruoma et al., "Applications and bioefficacy of the functional food supplement fermented papaya preparation," Toxicology, 278: 6-16 (2010).
Sen et al., "Human Skin Wounds: A Major and Snowballing Threat to Public Health and the Economy," Wound Repair and Regeneration, 17: 763-771 (2009).
Collard et al., "Improved function of diabetic wound-site macrophages and accelerated wound closure in response to oral supplementation of a fermented papaya preparation," Antioxidants & Redox Signaling, 13: 599-606 (2010).
Brown, "Control of respiration and ATP synthesis in mammalian mitochondria and cells," Biochemical Journal, 284: 1-13 (1992).
Ray, "Good ROS Versus Bad ROS," Science Signaling, 3: ec218 (2010).
Devaraj et al., "Effect of high-dose alpha-tocopherol supplementation on biomarkers of oxidative stress and inflammation and carotid atherosclerosis in patients with coronary artery disease," American Journal of Clinical Nutrition, 86: 1392-1398 (2007).
Somanah et al., "Relationship between fermented papaya preparation supplementation, erythrocyte integrity and antioxidant status in pre-diabetics," Food and Chemical Toxicology, 65: 12-17 (2014).
Dickerson et al., "Correction of Aberrant NADPH Oxidase Activity in Blood-Derived Mononuclear Cells from Type II Diabetes Mellitus Patients by a Naturally Fermented Papaya Preparation," Antioxidants & Redox Signaling, 17: 485-491 (2012).
International Search Report issued in corresponding International Patent Application No. PCT/JP2014/071810 dated Nov. 25, 2014.
Marotta et al., "Nutraceutical Supplementation: Effect of Fermented Papaya Preparation on Redox Status and DNA Damage in Healthy Elderly Individuals and Relationship with GSTM1 Genotype," Annals New York Academy of Sciences, 1067: 400-407 (2006).
Marotta et al., "Effect of a fermented papaya preparation on oxidative damage in cirrhosis," The Journal of Japan Mibyou System Association, 12 (1): 65-67 (2006) (see partial English translation).
International Preliminary Report on Patentability and Written Opinion issued in counterpart International Patent Application No. PCT/JP2014/071810 dated Mar. 2, 2017.
International Preliminary Report on Patentability and Written Opinion issued in International Patent Application No. PCT/JP2014/071809 dated Mar. 2, 2017.
Danese et al., "Plasma glucose level decreases as collateral effect of fermented papaya preparation and use," Clinical Therapeutics, 157 (3): 195-198 (2006).
Somanah et al., "Effects of a short term supplementation of a fermented papaya preparation on biomarkers of diabetes mellitus in a randomized Mauritian population," Preventive Medicine, 54: S90-S97 (2012).

* cited by examiner

METHOD OF TREATING TYPE 2 DIABETIC PATIENTS

TECHNICAL FIELD

The present invention relates to a respiratory burst activity promoter for promoting respiratory burst activity, and an immunostimulant. Specifically, the invention relates to a respiratory burst activity promoter for improving the production of reactive oxygen species (ROS) induced by NADPH oxidase and promoting respiratory burst activity in type 2 diabetic patients, comprising a fermented *papaya* preparation (FPP) as an active ingredient, and an immunostimulant, based on improving the production of reactive oxygen species (ROS) induced by NADPH oxidase and promoting respiratory burst activity in type 2 diabetic patients, comprising FPP as an active ingredient.

BACKGROUND ART

FPP produced by fermenting the unripe fruit of *Carica papaya* Linn together with sugar using edible yeast contains increased maltose and maltotriose in a mixture with saliva compared to that in a mixture with water.

The oral ingestion of FPP is expected to serve to imp rove the intestinal environment by increased oligosaccharides and also expected to suppress an increase in the blood glucose level and promote wound healing in type 2 diabetic patients (Patent Literature 1). FPP is also known to have an antioxidant property and be effective on symptoms associated with aging (Non Patent Literature 1).

A chronic wound is an important problem in health for diabetic patients (Non Patent Literature 2). The present inventors recently reported, for the first time, evidence that FPP had the possibility of particularly influencing macrophage response in the wound area and subsequent angiogenic response to improve the surface wound of diabetic patients (Non Patent Literature 3). The present inventors also showed that FPP promoted respiratory burst activity ex vivo in human peripheral blood mononuclear cells (PBMC) of patients with type 2 diabetes (T2D), resulting in NADPH oxidase-dependent improvement (Non Patent Literature 4).

ATP synthesis and mitochondrial respiration are two pathways forming the core of cellular metabolism. Respiration consists of the oxidation of mitochondrial NADPH by oxygen. The formation of NADPH by oxygen works in conjunction with the electron transport chain producing an electrochemical gradient of protons consisting of membrane potential and pH gradient (Non Patent Literature 5). The human peripheral blood mononuclear cells (PBMC) of patients with type 2 diabetes (T2D) result in a reduction in the respiratory burst activity, which increases the risk of infectious disease.

In recent years, the importance of two ROSs, i.e., "good ROS vs bad ROS" has also been in the spotlight (Non Patent Literature 6).

CITATION LIST

Patent Literature

Patent Literature 1: Japanese Patent Application Laid-Open No. 2011-041478

Non Patent Literature

Non Patent Literature 1: Aruoma O I, Hayashi Y, Marotta F, Mantello P, Rachmilewitz E, Montagnier L. Applications and bioefficacy of the functional food supplement fermented *papaya* preparation. Toxicology 278: 6-16, 2010.

Non Patent Literature 2: Sen C K, Gordillo G M, Roy S, Kirsner R, Lambert L, Hunt T K, Gottrup F, Gurtner G C, Longaker M T. Human Skin Wounds: A Major and Snowballing Threat to Public Health and the Economy. Wound Repair Regen in press, 2009.

Non Patent Literature 3: Collard E, Roy S. Improved function of diabetic wound-site macrophages and accelerated wound closure in response to oral supplementation of a fermented *papaya* preparation. Antioxid Redox Signal 13: 599-606, 2010.

Non Patent Literature 4: Dickerson R, Deshpande B, Gnyawali U, Lynch D, Gordillo G M, Schuster D, Osei K, Roy S. Correction of aberrant NADPH oxidase activity in blood-derived mononuclear cells from type II diabetes mellitus patients by a naturally fermented *papaya* preparation. Antioxid Redox Signal 17: 485-91, 2012.

Non Patent Literature 5: Brown G C. Control of respiration and ATP synthesis in mammalian mitochondria and cells. Biochem J 284 (Pt 1): 1-13, 1992.

Non Patent Literature 6: Ray LB. Good ROS Versus Bad ROS. Sci. Signal. 3: ec218, 2010.

SUMMARY OF INVENTION

Technical Problem

An object of the present invention is to confirm the safety of FPP in type 2 diabetic patients while determining its in vivo effect on respiratory burst in human peripheral-blood mononuclear cells to find further health advantages for the type 2 diabetic patients.

Solution to Problem

As a result of various studies for achieving the above object, the present inventors have found that FPP improves the production of reactive oxygen species (ROS) induced by NADPH oxidase and promotes respiratory burst activity in type 2 diabetic patients.

Thus, the present invention provides a respiratory burst activity promoter for improving the production of reactive oxygen species (ROS) induced by NADPH oxidase and promoting respiratory burst activity in type 2 diabetic patients, comprising FPP as an active ingredient. The invention also provides an immunostimulant, based on improving the production of reactive oxygen species (ROS) induced by NADPH oxidase and promoting respiratory burst activity in type 2 diabetic patients, comprising FPP as an active ingredient.

Advantageous Effects of Invention

According to the respiratory burst activity promoter of the present invention, respiratory burst activity can be promoted without adversely affecting the blood glucose level of patients with type 2 diabetes (T2D). This is useful for T2D patients since particularly in T2D patients in whom the respiratory burst activity is reduced, "good ROS" (respiratory burst) is promoted and "bad ROS" (oxidative stress) is removed. This enables an increase in the immunity of type 2 diabetic patients.

BRIEF DESCRIPTION OF DRAWINGS

FIG. 2 is a series of graphs showing that the oral ingestion of FPP had the effect of improving respiratory burst activity in peripheral-blood mononuclear cells of T2D patients. FPP improved the reduced respiratory burst activity induced by T2D but did not affect systemic oxidative stress. "A" indicates a fold change in superoxide anion production over base line, and data are presented as a mean±standard deviation (n=14). * indicates p<0.05. "B" indicates a change (%) in the protein carbonyl level over base line, and data are presented as a mean±standard deviation (n=10). "C" indicates a change (%) in the 4-hydroxynonenal (HNE-4) level over base line, and data are presented as a mean±standard deviation (n=17).

FIG. 4 is a series of graphs showing the effect of promoting mitochondrial membrane potential and oxygen consumption by FPP. "A" indicates the results of flow cytometry. "B" is a graph showing the ratio of depolarized cells to polarized cells (FL2-h/FL1-h); § indicates p<0.05 against glucose-depleted cells; and * indicates p<0.05 against NG "C" is a schematic of tracing the measurement of state IV and uncoupled respiration in NG and NG+FPP. "D" is a graph showing the ratio of uncoupled rate to state IV rate. * indicates p<0.05 against NG (n=3).

DESCRIPTION OF EMBODIMENTS

The respiratory burst activity promoter of the present invention comprises FPP as an active ingredient, and improves the production of reactive oxygen species (ROS) induced by NADPH oxidase and promotes respiratory burst activity in type 2 diabetic patients. The immunostimulant of the present invention comprises FPP as an active ingredient, and is based on improving the production of reactive oxygen species (ROS) induced by NADPH oxidase and promoting respiratory burst activity in type 2 diabetic patients.

As described above, FPP is a *papaya*-derived fermented product produced by fermenting the unripe fruit of *Carica papaya* Linn together with sugar using edible yeast.

It is preferable for FPP to be one produced by Osato Laboratory Inc. and sold by Osato International Inc. (Patent Literature 1 and Non Patent Literature 1). The FPP can be obtained as "FPP Fermented *papaya* Preparation" ® or "Immun' Age" ®. The FPP is produced in a factory receiving ISO 9001: 2008, ISO 14001: 2004, and ISO 22000: 2005 certifications and gaining the certification of FSSC 22000 as a most rigorous food safety standard in Europe and the United States as a first receiver in JIA, Japan, and is guaranteed in terms of quality, environment aspect, and safety.

The method for producing FPP is described, for example, in Patent Literature 1. According to analysis by Japan Food Research Laboratories, 91.2 g in 100 g of FPP is carbohydrate, and FPP also contains small amounts of protein (0.3 g), lipid (0.2 g), potassium (14.9 mg), and water (8.5 g) (lot. no. 091; analysis certificate dated May 27, 2014).

FPP may be properly prepared in various forms, such as granules, powders, and subtle granules in a manner suitable for oral ingestion, and, in preparation, additives, for example, an excipient, a binder, a lubricant, may be properly added.

The usage amount of FPP as an active ingredient may be 0.5 to 30 g/day per adult having a body weight of 70 kg, preferably 1 to 20 g/day, more preferably 3 to 15 g/day, most preferably 3 to 9 g/day.

The respiratory burst activity promoter of the present invention can promote respiratory burst activity without adversely affecting the blood glucose level of type 2 diabetic (T2D) patients in whom the respiratory burst activity is reduced. From this, health effects, such as immunopotentiation, can be expected in T2D patients. FPP is the world's first substance capable of enhancing immunity in diabetic patients without changing the blood glucose level despite being a carbohydrate. The basis therefor is that the substance increases respiratory burst activity by improving ROS production due to NADPH oxidase induction in diabetic patients.

EXAMPLES

[Materials and Methods]
(1) Human Subject and Sample Collection

The clinical trial in humans was approved by the institutional review board of Ohio State University (OSU). The adult subjects in the clinical trial were those who were clinically diagnosed as type 2 diabetes mellitus, had well-controlled glucose levels, and had an HbA1c value of 7% or less. The subjects were recruited in a diabetes clinic located in the Ohio State University Wexner Medical Center, and patients having a suppressed immune response or taking a peroxisomal proliferator-activated receptor-γ agent were excluded from the trial. Peripheral blood (60 cc) was collected by venipuncture, and 10 cc of the blood was sent to the Ohio State University Wexner Medical Center Clinical Laboratories and subjected to blood chemical examination. The remaining blood was used for the separation of peripheral-blood mononuclear cells (PBMC) and plasma. PBMC was promptly used for respiratory burst assay. The plasma from the patients was separated from the whole blood, centrifuged, snap-frozen in liquid nitrogen, and stored at −80° C. until all samples were collected, and the samples were subsequently analyzed together.

(2) Separation and Culture of Human Peripheral-Blood Mononuclear Cell

Fresh blood was 1:1 diluted with Dulbecco's phosphate buffered saline (DPBS; Gibco/Life Technologies, Carlsbad, Calif.). Human peripheral-blood mononuclear cells (PBMC) were separated by Ficoll density centrifugation and subsequent sorting with magnetic beads coated with anti-CD14 (Miltenyi Biotec, Auburn, Calif., USA).

(3) Measurement of Superoxide Anion

The promoted production of superoxide anion ($O_2^-$) was detected using a chemiluminescence LumiMax® superoxide anion measurement kit (Stratagene, La Jolla, Calif.) according to a maker-recommended protocol. The production of reactive oxygen species (ROS) in respiratory burst in PBMC was measured after stimulation with 1 μg/ml of phorbol myristate acetate (PMA). A human promyelocytic leukemia cell line (HL-60) was used as a control.

(4) Cell Culture

A human monocytic cell line, THP-1 cells, was cultured for 48 hours in RPMI1640 glucose-free medium (Life Technologies, Carlsbad, Calif.) containing 10% fetal bovine serum (FBS) and 1% antibiotic/antifungal agent (AA) to remove glucose from the cells. Then, to recover carbohydrate in the cells, the above glucose-free medium was supplemented by the following substrate: a normal glucose level (NG) (11 mM or 2 mg/mL glucose in the medium), a high glucose level (HG) (20 mM or 3.9 mg/mL glucose in the medium), FPP (2.9 mg/mL FPP in the medium), or NG+FPP (11 mM or 2 mg/mL glucose and 2.9 mg/mL FPP in the medium). The supplemented medium was subjected to sterile filtration with a 0.22-μm vacuum filter system (Millipore, Billerica, Mass., USA), and subsequently added to the THP-1 cells from which glucose was removed. The cells for the substance groups were cultured together with the respective substrates for 24 hours and subjected to assay.

HL-60 cells were cultured in high-glucose DMEM which contained sodium pyruvate (Life Technologies, Carlsbad, Calif., USA) and to which 20% FBS and 1% AA were added.

(5) Measurement of Metabolite and Oxidative Stress

The concentration of NADP/NADPH was measured using a NADP/NADPH quantification kit (Sigma-Aldrich, St. Louis, Mo., USA) according to a maker-recommended protocol. THP-1 cells were washed with cold DPBS after recovering carbohydrate for 24 hours. The cells were lysed by repeating 2 cycles of freezing and thawing. To remove an NADPH-consuming enzyme, the lysate was filtered using a 10-kDa ultrafiltration spin column (Amicon/Millipore, Billerica, Mass., USA). To detect NADPH, a sample containing total NADP was heated at 60° C. for 30 minutes and NADP was digested to leave only NADPH. The total NADP sample and the NADPH sample were incubated together with an NADP cycling enzyme at room temperature for 5 minutes to convert NADP to NADPH. A developer for colorimetric analysis was added to the sample, which was then incubated at room temperature for 1 hour. Absorption at 450 nm was measured using an automated microplate (Model Synergy 2, BioTek, Winooski, Vt., USA).

The ATP concentration was measured using an ATP assay kit (Abcam, Cambridge, Mass., USA) according to a maker-recommended protocol. THP-1 cells were washed with cold DPBS after recovering carbohydrate for 24 hours. Protein was removed from the sample using ice-cold 4 M perchloric acid (PCA). An equal amount of 2 M potassium hydroxide (KOH) was added to neutralize the sample to pH 6.8-7.2 to precipitate excess PCA. The sample was incubated for 30 minutes and subjected to colorimetric assay, and then absorption at 570 nm was measured.

Protein carbonyl was measured using Protein Carbonyl Content Assay Kit (Abcam, Cambridge, Mass., USA) according to a maker-recommended protocol.

4-Hydroxynonenal (HNE-4) was measured using OxiSelect™ HNE Adduct Competitive ELISA kit (Cell Biolabs, Inc. San Diego, Calif., USA) according to a maker-recommended protocol.

(6) Mitochondrial Membrane Potential Measurement

THP-1 cells were cultured together with cationic JC-1 dye (Life Technologies, Carlsbad, Calif.) capable of accumulating depending on the potential difference in mitochondria, for 20 minutes under conventional conditions. The polarized state of the cells cultured with the above substrate group was measured by measuring an emission shift from green (about 525 nm, FL1-H channel) to red (about 590 nm, FL2-H channel). The reduced emission ratio of red to green indicates depolarization or low membrane potential. The emission ratio of red to green entirely depends on the membrane potential and is not affected by the size, density, or shape of mitochondria. Measurements were collected using flow cytometry (model C6 Flow Cytometer, Accuri, Ann Arbor, Mich., USA) after 25 K events per sample.

(7) Oxygraph Measurement of Oxygen Consumption

To measure the consumption of oxygen ($O_2$), stage IV and uncoupled respirations were measured. Cells were subjected to permealization treatment using digitonin (4 μg/$10^6$ cells).

The respiratory medium contains 230 mM mannitol, 70 mM sucrose, 3 mM HEPES (pH 7.4), and 10 mM succinic acid ester. The succinic acid ester was first oxidized with complex II. Then, oligomycin (2 mM) was added to inhibit complex V (ATP synthase) to prevent the formation of ATP from endogenous ADP (state IV respiration). The maximal respiration was generated by adding carbonyl cyanide m-chlorophenylhydrazone (CCCP, 1.5 μM) as an uncoupling agent to chemically extinguish the membrane potential. Finally, antimycin A (1.5 mM) was added to suppress complex III. This limits the transfer of electrons to cytochrome c and the subsequent reduction of $O_2$ to $H_2O$ by complex IV, resulting in the suppression of oxygen consumption. The oxygen consumption rate was measured using a Clark's oxygen electrode and an oxygen monitor (Yellow Springs Instrument, Yellow Springs, Ohio, USA). Oxygen consumption was calculated by dividing the uncoupled rate by the state IV rate.

(8) Statistics

In vitro data are reported as the mean±standard error of triplicate to pentaplicate experiments. The comparison between a plurality of the groups was tested by variance analysis (ANOVA). $p<0.05$ indicates statistically significant difference. Data from 17 adult subjects (n=17) were presented for the human T2D trial (Table 1).

Example 1: Safety of FPP in T2D Patient

Before examining the in vivo effect of FPP in T2D patients, the safety of FPP in T2D patients was first confirmed.

In 17 patients diagnosed as T2D, blood before the start of FPP ingestion (base line (BL)) was collected in OSU Diabetic Clinic, and FPP (9 g/day) was ingested for subsequent 6 weeks, during which they came 2 times to the clinic. The test was completed by 2 times visiting to the clinic during subsequent wash-out. With every visiting to the clinic, respiratory burst ROS production, fasting blood glucose, lipid value, glycated hemoglobin (HbA1c), and lipid/protein peroxidation reaction were measured. Peripheral blood was collected from T2D patients in OSU Diabetic Clinic (see Table 1). For T2D patients, the period of 6-week FPP (9 g/day) ingestion and 2-week wash-out was provided.

TABLE 1

| Patient Statistics | |
|---|---|
| Total Number of Recruitments (n) | 22 |
| Number of Completed Study (n) | 17 |
| Age (Years) | 56.4 ± 12 |
| Gender-Males | 12 |
| Gender-Females | 10 |
| Ethnicity-White | 6 |
| Ethnicity-Black | 12 |
| Ethnicity-Asian | 4 |
| HbA1c (%) | 7 ± 0.8 |
| BMI (kg/$m^2$) | 32.8 ± 4.9 |

The return of an empty used bag for FPP was defined as patient's compliance, and the average compliance rate was 90%. Fasting blood glucose, glycated hemoglobin (HbA1c), and cholesterol levels were measured during base-line, ingestion, and wash-out.

Figure 1:
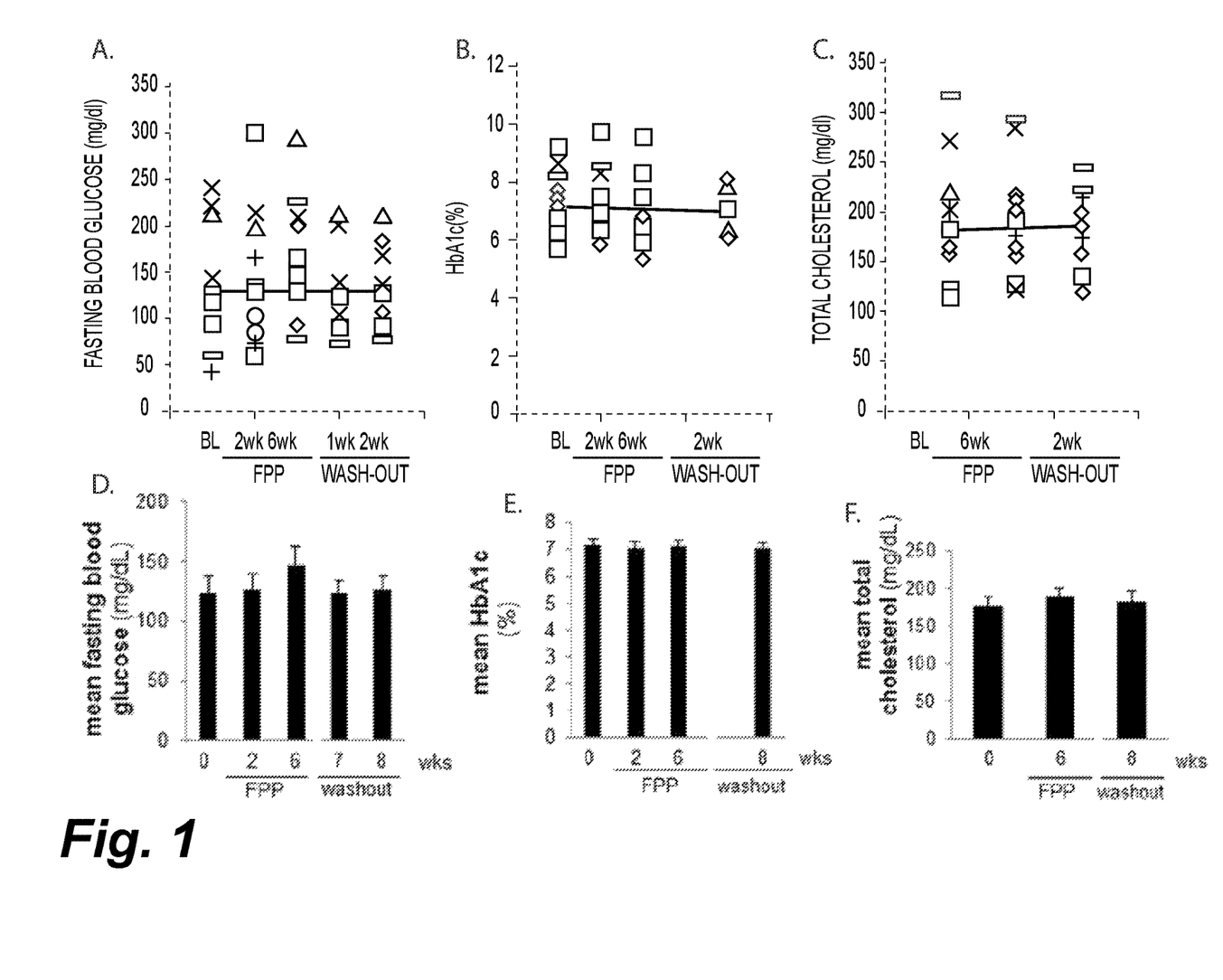
FIG. 1 is a series of graphs showing the results of confirming the safety of FPP in T2D patients. The oral ingestion of FPP little affected fasting blood glucose (A and D), HbA1c (B and E), or total cholesterol (C and F) in T2D patients. Data are presented as a mean±standard deviation (n=15).

The results are shown in FIG. 1. FIG. 1 suggested that since the ingestion of FPP did not affect blood glucose and total lipid levels, FPP could be safely ingested by T2D patients. As shown by the HbA1c level, no long-term effect on the blood glucose level was observed to be changed throughout this study period.

The oral ingestion of FPP remarkably induced respiratory burst ROS production in PBMC, while not affecting the blood components during ingestion. FPP has a long track record on the safety of human ingestion. This study has originality in terms of having, for the first time, investigated the influence of FPP on blood glucose, HbA1c, and total lipid levels in T2D patients. These results showed that FPP was high in tolerability for T2D patients despite its sweetness and its carbohydrate composition.

Example 2: Improvement of Respiratory Burst Activity in Peripheral-Blood Mononuclear Cell of T2D Patient by FPP The present inventors previously reported that the ex vivo treatment of human peripheral-blood mononuclear cells (PBMC) with FPP improved a reduction in respiratory burst due to T2D when stimulated with phorbol 12-myristate 13-acetate (PMA) (Non Patent Literature 4).

To verify whether or not the in vivo oral ingestion of FPP could improve respiratory burst activity in monocytes, peripheral-blood mononuclear cells (PBMC) were collected from T2D patients. PBMC were collected from T2D subjects during base-line, 2 and 6 weeks after starting the ingestion of FPP, and 2 weeks after wash-out. After stimulation with PMA (1 μg/ml) for 30 minutes, the production of reactive oxygen species (ROS) superoxide anion during respiratory burst in PBMC was measured by detection by chemiluminescence. Protein carbonyl and 4-hydroxynonenal (HNE-4) were measured by ELISA, as described above. The fresh plasma was one which was snap-frozen in liquid nitrogen, and stored until all samples were collected. All samples were simultaneously measured.

Figure 2:
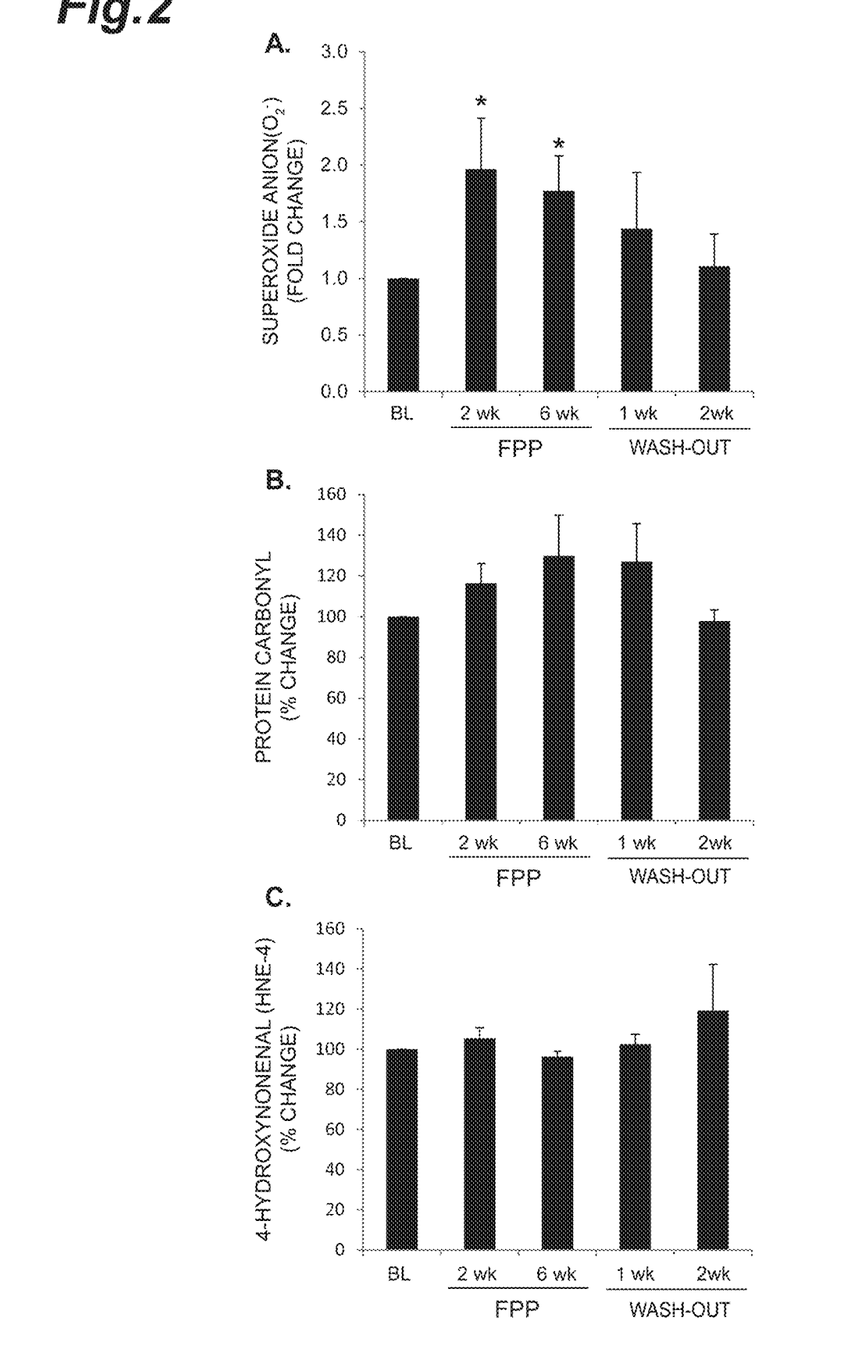

The results are shown in FIG. 2. It was revealed from FIG. 2 that the production of ROS was significantly promoted compared to that during base-line in the patients (A in FIG. 2). It was previously reported that the ingestion of α-tocopherol as an antioxidant decreased the release of superoxide anion in monocytes (Devaraj S, Tang R, Adams-Huet B, Harris A, Seenivasan T, de Lemos J A, Jialal I. Effect of high-dose alpha-tocopherol supplementation on biomarkers of oxidative stress and inflammation and carotid atherosclerosis in patients with coronary artery disease. Am J Clin Nutr 86: 1392-8, 2007).

To verify whether or not the production of ROS through NADPH oxidase due to FPP increased systemic oxidative stress, the influence of FPP on carbonyl protein and 4-hydroxynonenal (HNE-4) as a lipid peroxide reaction marker was measured with every visiting to the clinic. FPP increased necessary respiratory burst ROS in T2D patients but did not adversely affect oxidative stress throughout the FPP ingestion period (B to C in FIG. 2).

The oral ingestion of 6 g/day of FPP for 14 weeks was reported to significantly reduce the hemolysis rate and decrease the accumulation of protein carbonyl in the serum of patients with prediabetes (Somanah J, Bourdon E, Rondeau P, Bahorun T, Aruoma O I. Relationship between fermented *papaya* preparation supplementation, erythrocyte integrity and antioxidant status in pre-diabetics. Food Chem Toxicol 65: 12-7, 2014).

Based on these observations, the present inventors presume that the ingestion of FPP can improve innate immune response in diabetic patients.

Example 3: Promotion of Intracellular Production of ATP and NADPH by FPP

The hyperphosphorylation of oxidase subunit p47 (PHOX) occurs when NADPH oxidase is active in intact cells. The present inventors previously reported that p47 (PHOX) was upregulated in PBMC ex vivo given FPP.

As described in [Materials and Methods], the human monocytic cell line, THP-1 cells, was cultured in the glucose-free medium for 48 hours, and, after removing glucose from the cells, cultured for 24 hours in a medium containing a normal glucose level (NG), a high glucose level (HG), FPP, or NG+FPP. Thereafter, the cells for the substance groups were measured for intracellular ATP, NADP, and NADPH by ELISA.

Figure 3:
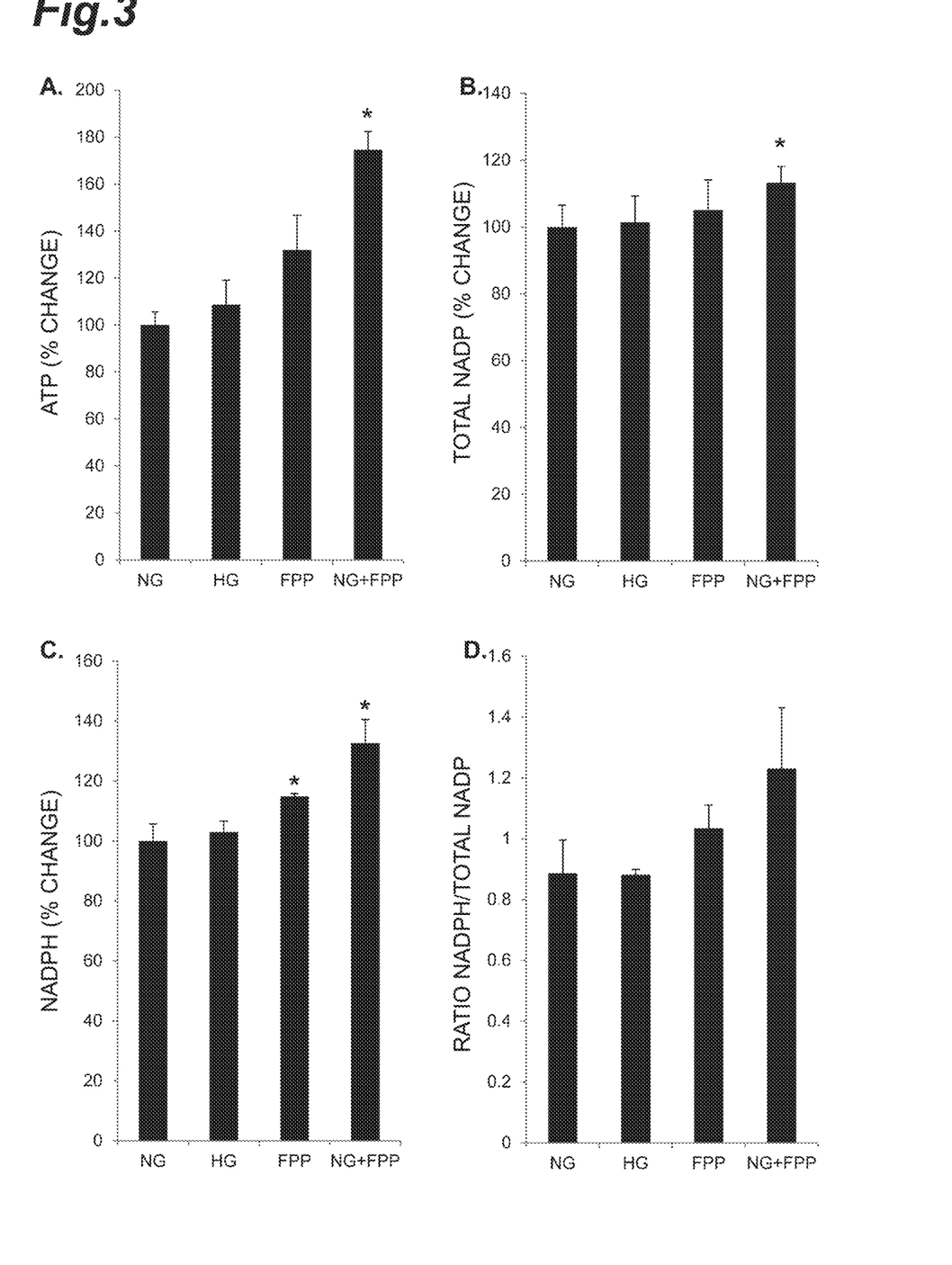
FIG. 3 is a series of graphs showing the effect of promoting intracellular ATP and NADPH production by FPP. Data are presented as a mean±standard deviation (n=4). * indicates p<0.05 against NG

The results are shown in FIG. 3. ATP is necessary for phosphorylation reaction. In the human monocytic cell line, THP-1 cells, the ATP level was 75% higher for the glucose medium containing FPP (NG+FPP) than that for only the glucose medium (NG), suggesting that FPP promoted ATP production in the monocytes (A in FIG. 3). These results are unexpected and new in that the sweet dietary supplement can increase intracellular ATP production. Since the same results were not observed for the high glucose medium (HG), it was suggested that the increase in the ATP level did not depend on glucose contained in FPP and a particular component in FPP promoted the intracellular production of ATP in monocytes.

NADPH oxidase in leukocytes consumes NADPH to catalyze superoxide anion production. Interestingly, the treatment of THP-1 cells with FPP only slightly increased total NADP but increased the NADPH level of the cells by 30% (B to C in FIG. 3).

A dramatic transition was observed in the percentage of NADPH in NADPH/NADP, and it was suggested the possibility that the increased production of respiratory burst ROS through NADPH oxidase in T2D is a consequence of the increased level of ATP and NADPH in the cells (D in FIG. 3).

These results suggested that FPP promoted NADPH oxidase activity by increasing cellular ATP and NADPH levels.

Example 4: Increase in Mitochondrial Membrane Potential and Respiratory Activation by FPP ATP synthesis and mitochondrial respiration are two pathways forming the core of cellular metabolism. Respiration consists of the oxidation of mitochondrial NADPH by oxygen. The formation of NADPH by oxygen works in conjunction with the electron transport chain producing an electrochemical gradient of protons consisting of membrane potential and pH gradient.

ATP synthesis in mitochondria works in conjunction with ATP synthesis in the matrix of mitochondria by the penetration of protons into the membrane. ATP (adenosine triphosphate) is the major energy source for cells, and used for processes in most principal cells, including respiratory burst by NADPH oxidase.

To verify whether the ATP level of cells increases due to mitochondrial membrane potential (MMP) and respiration, the mitochondrial membrane potential was measured. As in Example 3, the human monocytic cell line, THP-1 cells, was cultured in the glucose-free medium for 48 hours, and, after removing glucose from the cells, cultured for 24 hours in a medium containing a normal glucose level (NG), a high glucose level (HG), FPP, or NG+FPP. Thereafter, the cells for the substance groups were measured for mitochondrial membrane potential and oxygen consumption as described in [Materials and Methods]. The mitochondrial membrane potential was measured by JC-1 dye and flow cytometry.

Figure 4:
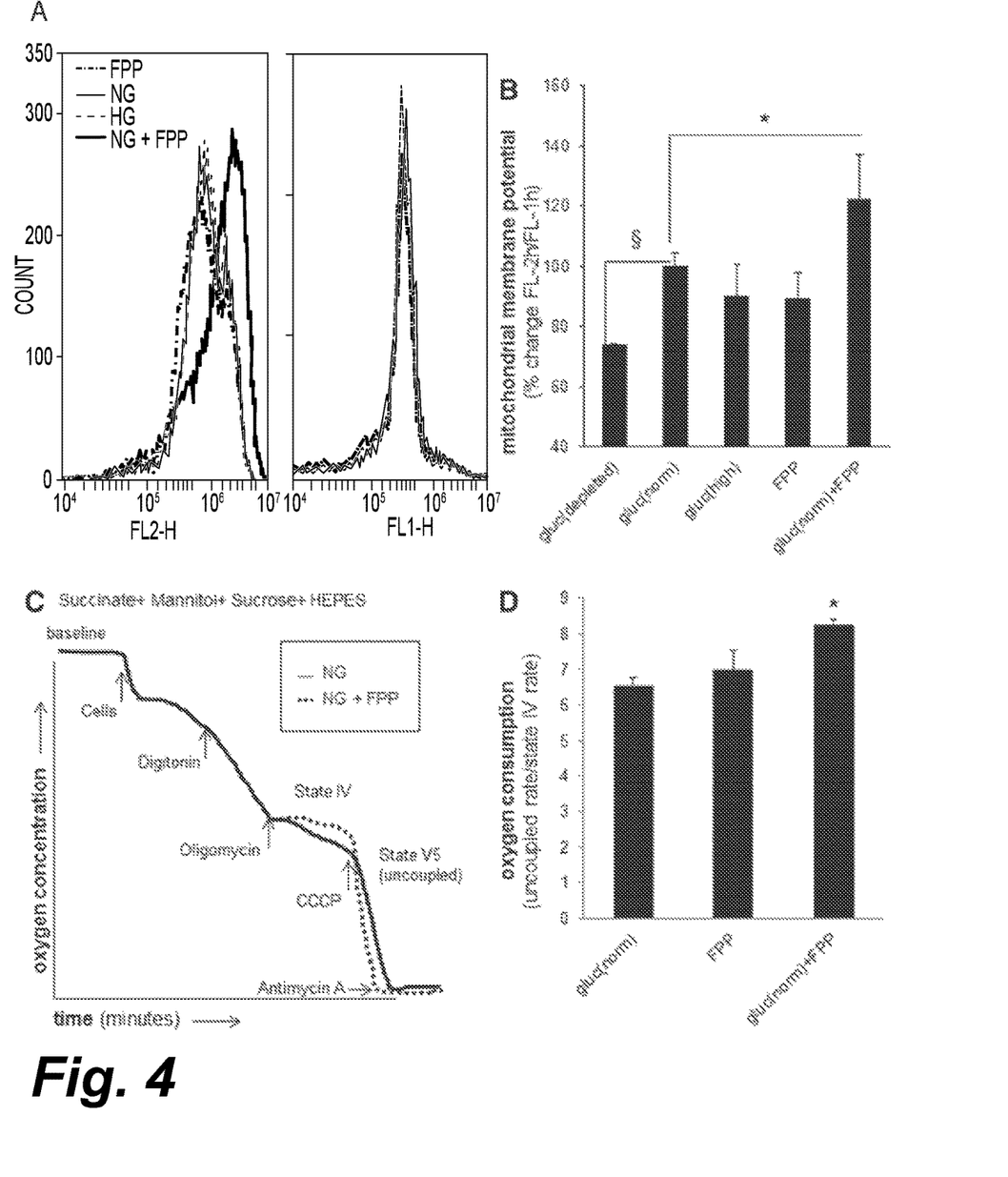

The results are shown in FIG. 4. An increase in red fluorescence emission was observed in the group of monocytic cells cultured under conditions of FPP and the normal glucose level (NG+FPP) (A in FIG. 4). An about 20% increase in MMP was observed in monocytic cells cultured under conditions of NG+FPP compared to that in monocytic cells cultured under conditions of the normal glucose level containing no FPP (NG) (B in FIG. 4).

To support the hypothesis of the present inventors that the administration of FPP increases mitochondrial respiration and thereby increases ATP production, the oxygen consumption of monocytic cells in the presence and absence of FPP administration was measured using a Clark's oxygen electrode monitor (C in FIG. 4).

The ratio of the uncoupled respiration rate to the state IV respiration rate for NG+FPP increased compared to that for NQ showing that the oxygen consumption of the cultured cells increased (D in FIG. 4).

Taken together, FPP may increase the supply of ATP and NADPH by activating mitochondrial respiration, resulting in the promotion of respiratory burst in PBMC of T2D patients. FPP has a long history, during which it has been safely consumed by humans; with reference to the clinical data from this study, FPP is expected to be effective on innate immune responses in T2D patients.

In diabetes, the blood glucose level increases since abnormal glucose metabolism fails to convert glucose in the body to energy, and thus peripheral circulation is made poor and immunity is depressed. This clinical study was the world's first clinical study directed, for the first time, toward an improvement in immunity and an enhancement in energy metabolism using FPP despite that FPP was made of carbohydrate. In addition, the present inventors present the new results that FPP stimulates mitochondrial respiration and promotes cellular ATP production without adversely affecting the blood glucose level of T2D patients.

A previous paper has reported that FPP has the possibility of having antioxidant activity. In recent years, the importance of two ROSs, i.e., "good ROS vs bad ROS" has also been in the spotlight (Non Patent Literature 6). FPP is given to significantly improve respiratory burst activity in monocytes. The possibility is also presented for the first time that FPP may be useful for T2D patients by serving two purposes in the physiological function of reactive oxygen species (ROS), i.e., promoting "good ROS" (respiratory burst) and removing "bad ROS" (oxidative stress).

The invention claimed is:

1. A method of promoting respiratory burst activity in a subject with type 2 diabetes without affecting blood glucose and total lipid levels of the subject with type 2 diabetes, the method comprising orally administering to the subject an effective amount of a fermented papaya preparation comprising:
   91.2% carbohydrate,
   3% protein,
   2% lipid,
   0149% potassium, and
   water,
   wherein the fermented papaya is the only anti-diabetic ingredient administered to the subject,
   the effective amount of the fermented papaya preparation is 9 g/day per adult having a body weight of 70 kg, and
   the method increases a production of reactive oxygen species (ROS) in the subject.

2. The method of claim 1, wherein the effective amount of the fermented *papaya* preparation improves the production of reactive oxygen species (ROS) induced by NADPH oxidase and promote respiratory burst activity.

3. The method of claim 1, wherein the effective amount of the fermented *papaya* preparation promotes respiratory burst activity without adversely affecting a blood glucose level of the subject.

4. The method of claim 1, wherein the fermented *papaya* preparation comprises *Carica papaya* Linn fermented with sugar.

5. The method of claim 1, wherein the fermented *papaya* preparation comprises *Carica papaya* Linn fermented with sugar using edible yeast.

6. The method of claim 1, wherein the fermented *papaya* preparation further comprises an excipient.

7. The method of claim 1, wherein the fermented *papaya* preparation further comprises a binder.

8. The method of claim 1, wherein the fermented *papaya* preparation further comprises a lubricant.

9. The method of claim 1, wherein the fermented *papaya* preparation comprises unripe fruit of *Carica papaya* Linn fermented with sugar using edible yeast.

10. A method of promoting respiratory burst activity in a subject with type 2 diabetes without affecting blood glucose and total lipid levels of the subject with type 2 diabetes, the method comprising orally administering to the subject an effective amount of *Carica papaya* Linn fermented with sugar,
    wherein the effective amount of the fermented papaya preparation is 9 g/day per adult having a body weight of 70 kg, and
    the method increases a production of reactive oxygen species (ROS) in the subject.

11. The method of claim 10, wherein the *Carica papaya* Linn is *Carica papaya* Linn fermented with sugar using edible yeast.

* * * * *